United States Patent
Wong

(10) Patent No.: US 9,619,882 B2
(45) Date of Patent: Apr. 11, 2017

(54) CORRELATED DIFFUSION IMAGING SYSTEM AND METHOD FOR IDENTIFICATION OF BIOLOGICAL TISSUE OF INTEREST

(71) Applicant: Alexander Sheung Lai Wong, Waterloo (CA)

(72) Inventor: Alexander Sheung Lai Wong, Waterloo (CA)

(*) Notice: Subject to any disclaimer, the term of this patent is extended or adjusted under 35 U.S.C. 154(b) by 412 days.

(21) Appl. No.: 14/309,318

(22) Filed: Jun. 19, 2014

(65) Prior Publication Data
US 2015/0371384 A1    Dec. 24, 2015

(51) Int. Cl.
*A61B 6/00* (2006.01)
*G06T 7/00* (2017.01)
*A61B 8/08* (2006.01)

(52) U.S. Cl.
CPC .......... *G06T 7/0016* (2013.01); *A61B 6/5205* (2013.01); *A61B 8/5207* (2013.01);
(Continued)

(58) Field of Classification Search
CPC . G06T 2207/30096; G06T 2207/10081; G06T 2207/10088; G06T 2207/10092; G06T 2207/10096; G06T 2207/10132; G06T 2207/20104; G06T 2207/20212; G06T 11/005; G06T 7/00; G06T 7/0016;
(Continued)

(56) References Cited

U.S. PATENT DOCUMENTS 5,317,262 A * 5/1994 Moonen ........... G01R 33/56341
324/306
6,389,097 B1 * 5/2002 Bulkes ................... A61B 6/032
378/15
(Continued)

*Primary Examiner* — Sumati Lefkowitz
*Assistant Examiner* — Carol Wang
(74) *Attorney, Agent, or Firm* — Tai W. Nahm; Miller Thomson LLP

(57) ABSTRACT

There is disclosed a novel form of imaging referred to in this disclosure as "correlated diffusion imaging" or CDI in which the tissue being imaged is characterized by a joint correlation of diffusion signal attenuation across multiple gradient pulse strengths and timings. Advantageously, by taking into account signal attenuation at different water diffusion motion sensitivities, correlated diffusion imaging can provide significantly improved delineation between cancerous tissue and healthy tissue when compared to existing diffusion imaging modalities. In an embodiment, the method comprises performing quantitative evaluation using receiver operating characteristic (ROC) curve analysis, tissue class separability analysis, and visual assessment to study correlated diffusion imaging for the task of identification of biological tissue of interest. In another embodiment, the method comprises comparing T2-weighted imaging results with that obtained using standard diffusion imaging (via the apparent diffusion coefficient (ADC)) and with that obtained using CDI for tissue characterization and analysis. In still another embodiment, the method comprises of a dual-stage signal mixing configuration of CDI that provides better visualization of anatomical information while preserving strong delineation between cancerous tissue and healthy tissue.

20 Claims, 9 Drawing Sheets

(52) U.S. Cl.
CPC ............... *G06T 2207/10081* (2013.01); *G06T 2207/10088* (2013.01); *G06T 2207/10132* (2013.01); *G06T 2207/20104* (2013.01); *G06T 2207/30081* (2013.01); *G06T 2207/30096* (2013.01)

(58) Field of Classification Search
CPC ....... A61B 5/00; A61B 5/0013; A61B 5/0033; A61B 2090/374
See application file for complete search history.

(56) References Cited

U.S. PATENT DOCUMENTS

| | | | |
|---|---|---|---|
| 2003/0214290 A1* | 11/2003 | van Muiswinkel | G01R 33/56341 324/307 |
| 2008/0234574 A1* | 9/2008 | Hancock | A61B 5/0507 600/430 |
| 2008/0310696 A1* | 12/2008 | Hwang | G01R 33/56341 382/131 |
| 2010/0308821 A1* | 12/2010 | Poupon | G01R 33/56341 324/309 |
| 2011/0254548 A1* | 10/2011 | Setsompop | G01R 33/4835 324/309 |
| 2012/0280686 A1* | 11/2012 | White | G01R 33/48 324/309 |
| 2013/0041260 A1* | 2/2013 | Schmidt | A61B 8/0825 600/442 |
| 2013/0266197 A1* | 10/2013 | Nagenthiraja | G06T 7/0012 382/128 |

* cited by examiner

CORRELATED DIFFUSION IMAGING SYSTEM AND METHOD FOR IDENTIFICATION OF BIOLOGICAL TISSUE OF INTEREST

FIELD OF THE INVENTION

The present invention relates generally to the field of medical imaging, and more particularly to a system and method for identification of biological tissue of interest utilizing improved imaging technologies and image processing techniques.

BACKGROUND

Various imaging technologies may be used to create detailed images of internal organs and internal physical features. For example, ultrasound utilizes high frequency sound waves that are reflected by internal tissue at different intensities to produce images viewable in real-time on a computer display. Ultrasound is commonly used for safely imaging a developing foetus in a pregnant woman, for example. Thermography utilizes differences in regional temperatures to create an infrared digital image of tissue, and is sometimes used in screening breast tissue for identification of potentially cancerous breast tumours. Tomography utilizes x-rays to provide imaging of a single plane or slice of tissue. One type of tomography is a Computed Axial Tomography scan (more commonly known as a CAT scan) which utilizes helical tomography to produce a series of thin slice or section images of a body to generate a virtual three-dimensional image of the inside of a body. While effective for screening certain types of tissues inside the body, existing imaging technologies and image processing techniques are still limited when it comes to screening for certain types of tissues located deep within the body which are substantially similar to the surrounding tissue.

Detection and localization of prostate cancer is one such challenge. Prostate cancer is the most common form of cancer diagnosed in men, with roughly 241,740 new cases in 2012 in the United States alone. Furthermore, prostate cancer is the second leading cause of cancer death in males in the United States, with an estimated 28,170 deaths in 2012. Similar per capita rates of deaths from prostate cancer can be found in other jurisdictions. Given that the median patient survival time for metastatic prostate cancer ranges from about 12.2 to 21.7 months, early clinical diagnosis of prostate cancer is key to improving the treatment and longevity of patients affected by prostate cancer.

Presently, conventional clinical diagnosis of prostate cancer involves a prostate specific antigen (PSA) screening, where high PSA levels are considered indicative of possible signs of prostate cancer. However, PSA screening has resulted in significant over-diagnosis of men suspected of having prostate cancer but who do not actually require treatment. As a consequence, many men are over-treated with therapies that carry significant risks in themselves. Furthermore, there is still no reliable, widely accepted method of diagnostic imaging for prostate cancer. Although transrectal ultrasound (TRUS) is used routinely as a guide for biopsy, it cannot be used to visualize cancer foci because many tumours in the prostate gland are isoechoic and cannot be easily differentiated from surrounding tissue, resulting in sensitivity and specificity in the range of only around 40-50%. Positron emission tomography (PET) have also been investigated as a potential imaging modality for prostate cancer detection, with a number of different tracers that have shown promise for identifying prostate cancer. However, the spatial resolution achieved using PET may not be adequate to properly localize and detect early stage prostate cancer. T2-weighted magnetic resonance imaging (MRI) has also been investigated for prostate cancer detection, but currently requires highly-qualified subspecialty radiologists to interpret the data due to its weak delineation between cancerous tissue and healthy tissue. Furthermore, in the peripheral zone of the prostate gland, the low T2 signal intensity that is associated with prostate cancer may also be due to a number of noncancerous abnormal conditions such as inflammation and hemorrhaging.

If detected at an early stage, the prognosis for recovery from prostate cancer is excellent. Hence, early detection and the localization of prostate cancer is crucial for diagnosis, as well as treatment via targeted focal therapy. Therefore, what is needed are further improvements in identification of tissues of interest utilizing novel imaging technologies and image processing techniques.

SUMMARY

The present invention relates to a system and method for identification of biological tissue of interest utilizing improved imaging technologies and image processing techniques. In an aspect, a new form of imaging is introduced and referred to in this disclosure as "correlated diffusion imaging" or CDI. With CDI, the tissue being imaged is characterized by a joint correlation of diffusion signal attenuation across multiple gradient pulse strengths and timings. Advantageously, by taking into account signal attenuation at different water diffusion motion sensitivities, correlated diffusion imaging can provide significantly improved delineation between cancerous tissue and healthy tissue when compared to existing diffusion imaging modalities.

In an embodiment, the method comprises performing quantitative evaluation using receiver operating characteristic (ROC) curve analysis, tissue class separability analysis, and visual assessment to study correlated diffusion imaging for the task of identification of biological tissue of interest.

In another embodiment, the method comprises comparing T2-weighted imaging results with that obtained using standard diffusion imaging (via the apparent diffusion coefficient (ADC)) and with that obtained using CDI for tissue characterization and analysis. Experimental results suggest that CDI can provide significantly improved delineation between healthy tissue and cancerous tissue based on signal attenuation of the tissue at different water diffusion motion sensitivities. This has significant potential as a diagnostic tool for cancer detection and localization, such as cancerous tissue in the prostate gland.

In still another embodiment, the method comprises of a dual-stage signal mixing configuration of CDI that provides better visualization of anatomical information while preserving strong delineation between cancerous tissue and healthy tissue.

In still another aspect, CDI may be implemented as a diagnostic medical device which may be utilized as an aid in the detection and localization of cancer.

In this respect, before explaining at least one embodiment of the invention in detail, it is to be understood that the invention is not limited in its application to the details of construction and to the arrangements of the components set forth in the following description or the examples provided therein, or illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

The present invention will be better understood and objects of the invention will become apparent when consideration is given to the following detailed description thereof. Such description makes reference to the annexed drawings wherein.

Figure 1:
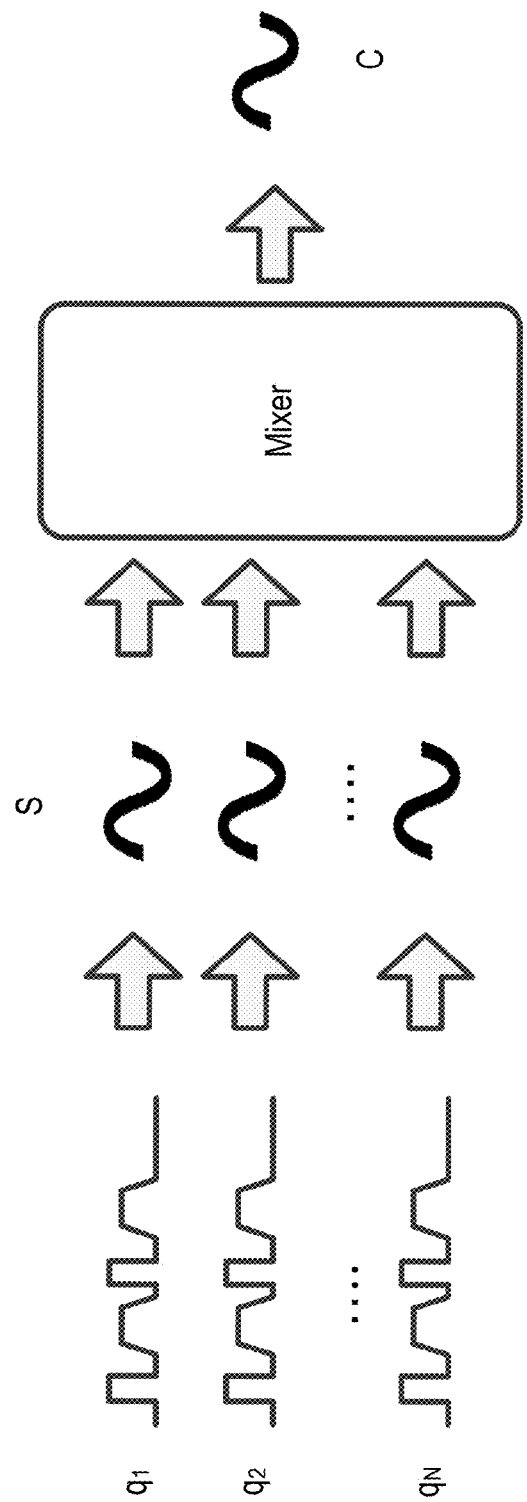
FIG. 1 shows an illustrative method of performing correlated diffusion imaging (CDI) in accordance with an embodiment.

In the drawings, embodiments of the invention are illustrated by way of example. It is to be expressly understood that the description and drawings are only for the purpose of illustration and as an aid to understanding, and are not intended as a definition of the limits of the invention.

DETAILED DESCRIPTION

As noted above, the present invention relates to a system and method for identification of biological tissue of interest utilizing improved imaging technologies and image processing techniques, termed herein as correlated diffusion imaging.

Diffusion imaging is a promising imaging modality for diagnosing cancer has been developed in which pairs of opposing magnetic field gradient pulses are applied to obtain sensitivity to the Brownian motion of water molecules in tissues. The differences in diffusion characteristics between tissue types facilitate for tissue characterization. As such, given the presumed high cellular density of prostate cancer, the associated tissues should exhibit restricted diffusion characteristics (and as such should have lower apparent diffusion coefficient (ADC) values). While diffusion imaging shows considerable promise, particularly when used in multi-parametric imaging scenarios, delineating between cancerous tissue and healthy tissue in the prostate gland remains a challenge, due partly to the necessity for fine-tuning the strength, duration, and timing of the applied diffusion gradient pulses. Hence, the characteristics between cancerous tissue and healthy tissue may appear to have substantial overlap depending on the way the gradient pulses are applied, thus making it difficult to detect and localize cancer. As such, an alternative form of magnetic resonance imaging that gets around this issue is highly desired.

As will now be described in detail, the presented system and method introduces a new form of diffusion magnetic resonance imaging referred to in the present disclosure as correlated diffusion imaging (CDI), which takes advantage of the joint correlation in signal attenuation across multiple gradient pulse strengths and timings to not only reduce the dependency on the way diffusion gradient pulses are applied, but also improve delineation between cancerous and healthy tissue. To the best of the inventor's knowledge, there are no previous imaging techniques that take this novel approach to cancer assessment. Illustrative embodiments of the system and method will now be described. First, the materials and methods underlying CDI are described in the Method Section below.

Method

In an illustrative example, the methodology behind correlated diffusion imaging (CDI) is summarized in FIG. 1. First, multiple signal acquisitions are conducted from a subject at different gradient pulse strengths and timings. Second, the acquired signals (and any interpolated and/or extrapolated signals) are then mixed together to produce a final signal that characterizes the tissue being imaged. A detailed description of the steps involved in the methodology is presented below.

Imaging Protocol

In one embodiment of CDI as a specific example for illustrating and evaluating the effectiveness of CDI for prostate cancer diagnosis, twenty patient cases with known prostate cancer were used as part of the study. The patients ranged in age from 58-80 years, with a median age of 69 years. Informed consent was obtained from all patients, and approval for the study was obtained from the ethics review board of Sunnybrook Health Sciences Centre, located in Toronto, Canada. All results were reviewed by an expert radiologist with 16 years of experience interpreting body MRI and 11 years of experience interpreting prostate MRI.

Examinations using CDI were performed using a Philips Achieva 3.0T machine at the Sunnybrook Health Sciences Centre. In this specific example embodiment, the axial echo-planar sequence was performed for CDI with the following imaging parameters: TR range from 3336-6178 ms with a median of 4890 ms, and TE ranged from 61-67 ms with a median of 61 ms. The resolution of the signal acquisitions ranged from $1.36 \times 1.36$ mm$^2$ to $1.67 \times 1.67$ mm$^2$ with a median of $1.56 \times 1.56$ mm$^2$. Slice thickness ranged from 3.0-4.0 mm with a median of 3.5 mm. The display field of view (DFOV) ranged from $20 \times 20$ cm$^2$ to $24 \times 24$ cm$^2$ with a median of $24 \times 24$ cm$^2$. The invention is capable of other embodiments and of being practiced with other MRI machines.

For comparison purposes, apparent diffusion coefficient (ADC) maps were also obtained using the same axial echo-planar sequence with the same imaging parameters and $\Omega = \{0 \text{ s/mm}^2, 100 \text{ s/s/mm}^2, 1000 \text{ s/mm}^2\}$, as it is considered state-of-the-art for prostate cancer analysis in existing diffusion imaging. Finally, axial T2-weighted imaging acquisitions with the same slice locations as the CDI sequence were obtained as a baseline reference of comparison. Examinations using T2-weighted imaging were performed using a Philips Achieva 3.0T machine with the following imaging parameters: TR range from 4688-7504 ms with a median of 6481 ms, and TE range from 110-120 ms with a median of 120 ms. Slice thickness ranged from 3.0-4.0 mm with a median of 3.5 mm. The display field of view (DFOV) ranged from 20×20 cm² to 24×24 cm² with a median of 24×24 cm².

Signal Acquisition

Figure 2:
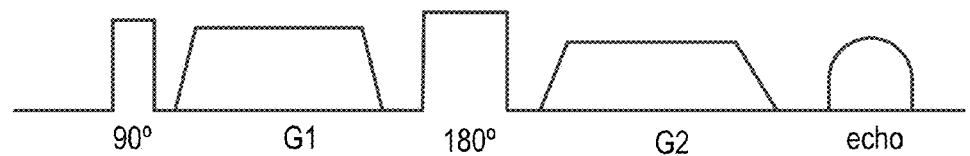
FIG. 2 shows an illustrative echo-planar sequence with two gradient pulses in accordance with an embodiment.

In an embodiment, as a first step of the CDI imaging process, axial single-shot echo-planar sequences with two gradient pulses of equal magnitude (one pulse in each side of the 180° pulse to dephase and rephase the spins, respectively), as shown in FIG. 2 are used to obtain multiple signal acquisitions using a set of different configurations of gradient pulse strengths and timings, which we will denote as $\Omega = \{q_i | i=1, \ldots, N\}$ where $q_i$ denotes the $i^{th}$ sequence. It will be appreciated, however, that other sequences may be used in alternative embodiments, including for example multi-shot echo-planar sequences and interleaved echo-planar sequences.

Imperfect rephasing occurs due to motion of water molecules, leading to attenuation in the acquired signal and thus allowing for the study of water diffusion based on signal attenuation behavior. By varying the configuration of gradient pulse strengths and timings between signal acquisitions, each signal acquisition is sensitive to a different degree of Brownian motion of water molecules in tissues, thus providing unique information with respect to the water diffusion characteristics of the tissue being imaged. The different configurations of gradient pulse strengths and timings can be defined by the following set of parameters:

$$q_i = (G_i, \delta_i, \Delta_i), \quad (1)$$

where, for the $i^{th}$ sequence, $G_i$ denotes the gradient pulse strength, $\delta_i$ denotes the gradient pulse duration, and $\Delta_i$ denotes time between gradient pulses. By grouping the gradient terms, the configuration of gradient pulse strengths and timings used for a particular sequence $q_i$ can be simplified to $$q_i = \gamma^2 G_i^2 \delta_i^2 \left(\Delta_i - \frac{\delta_i}{3}\right), \quad (2)$$

where $\gamma$ denotes the proton gyromagnetic ratio.

Signal Mixing

As the second step of the CDI imaging process, the multiple signal acquisitions are mixed together to obtain the final signal that characterizes the tissue being imaged. Here, of interest is not the signal attenuation obtained using the individual configurations of gradient pulse strengths and timings, but rather in the local correlation of signal attenuation across the different configurations of gradient pulse strengths and timings within a local spatial sub-volume V to provide a better overall characterization of the water diffusion properties of the tissue being imaged. As such, it is desirable to mix all of the signal acquisitions together into a single quantitative signal characterizing the local signal attenuation correlation. It will be appreciated that the implementation of the present system and method is not limited to mixing signal acquisitions together, as interpolated and/or extrapolated signals based on signal acquisitions may also be mixed with the signal acquisitions together in other embodiments.

To achieve this goal, the following signal mixing function $C(x)$ is introduced for characterizing local signal attenuation correlation, which is parameterized by diffusion range defined by $[q_\alpha, q_\beta]$ and is defined as $$C_{[q_\alpha q_\beta]}(x) = \int \ldots \int S_{q_\alpha}(x)^{\rho_\alpha} \ldots S_{q_\beta}(x)^{\rho_\beta} \\ f(S_{q_\alpha}(x), \ldots, S_{q_\beta}(x), V(x)) dS_{q_\alpha}(x) \ldots dS_{q_\beta}(x), \quad (3)$$

where x denotes spatial location, S denotes the acquired signal, $\rho_\alpha, \ldots, \rho_\beta$ denotes scaling factors, $f$ denotes a function that relates $Sq_\alpha(x), \ldots, Sq_\beta(x)$ within the sub-volume around x (denoted by $V(x)$). In this embodiment, the function $f$ is set as the conditional joint probability (e.g. $f(Sq_\alpha(x), \ldots, Sq_\beta(x) | V(x)))$. It will be appreciated, however, that the implementation of the present system and method is not limited to this particular function $f$, and other functions may be used for $f$ in other embodiments.

For the embodiment of CDI used in this study, $[q_\alpha, q_\beta]$ was set at [0 s/mm², 2000 s/mm²], and V was defined as a 7 mm³ spatial sub-volume for assessment purposes as it was found to provide good tissue delineation.

Image Analysis and Interpretation

In experimentation conducted by the inventor, the ADC maps and CDI images were reconstructed using the Pro-CanVAS (Prostate Cancer Visualization and Analysis System) platform developed at the University of Waterloo Vision and Image Processing research group, and were analyzed such that each modality was analyzed independent of other modalities. All visual assessments were made by an expert radiologist with 16 years of experience interpreting body MRI and 11 years of experience interpreting prostate MRI. The invention is capable of other embodiments and of being practiced with other image visualization platforms.

Statistical Analysis

Two different analysis strategies were performed to quantify the potential of CDI as a tool for prostate cancer detection and localization. In the first analysis strategy, a receiver operating characteristic (ROC) curve analysis was performed using CDI to quantitatively assess prostate detection and localization. The ROC curves were estimated assuming bivariate normal data. For illustrative purposes, the ROC curves obtained from the pooled data of all patient cases was plotted. To provide a quantitative assessment of diagnostic accuracy, the area under the ROC curve ($A_Z$) was obtained as a single metric of diagnostic accuracy. For comparison purposes, ROC curve analysis was also performed using ADC map as the baseline reference method for assessing prostate cancer using diffusion imaging.

In the second analysis strategy, the inventor studied whether CDI would be a useful imaging modality for building computer-aided clinical decision support systems to assist in the prostate cancer detection and localization process. To quantify the usefulness of CDI for the purpose of building such systems, leave-one-out cross-validation (LOOCV) trials were performed across all patient cases. For each trial, a two-class Maximum Likelihood (ML) classifier model is trained based on the CDI signal intensity statistics of the individual voxels within the prostate gland (one class characterizing cancerous tissue, with the other class characterizing healthy tissue) across the training patient cases. This learned two-class ML classifier model is then used to calculate sensitivity, specificity, and accuracy for the validation patient case. This process is repeated for a number of trials so that each patient case is used once as the validation patient case. The same was performed on ADC for comparative purposes.

Results

Figure 3:
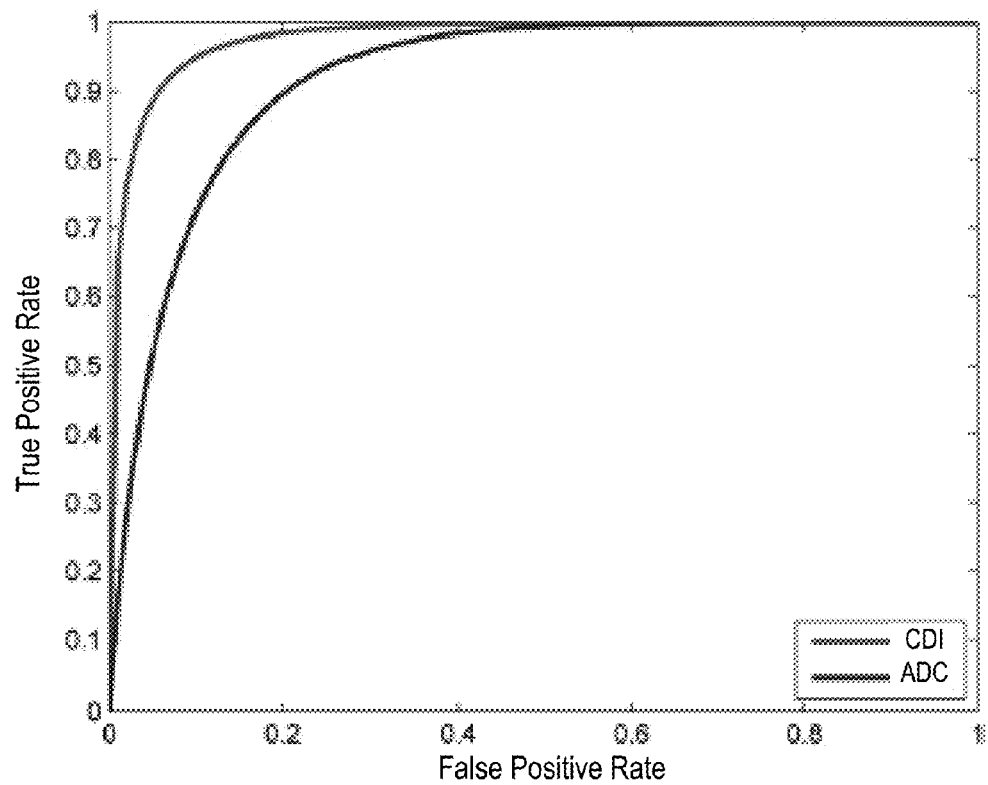
FIG. 3 shows illustrative receiver operator characteristic (ROC) curves in accordance with an embodiment.
Figure 4:
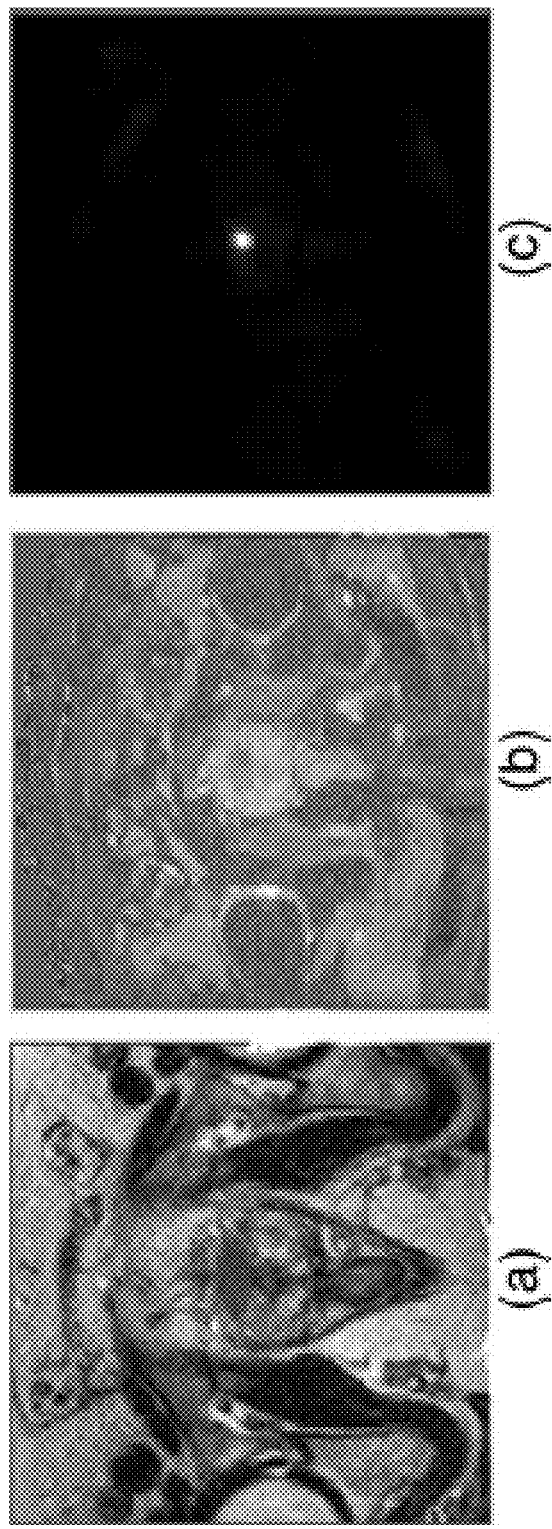
FIGS. 4(a) and 4(b) show illustrative results obtained from prior art digital imaging techniques, in comparison to FIG. 4(c) which shows an illustrative digital image of potentially cancerous tissue acquired through CDI in accordance with embodiment.
Figure 5:
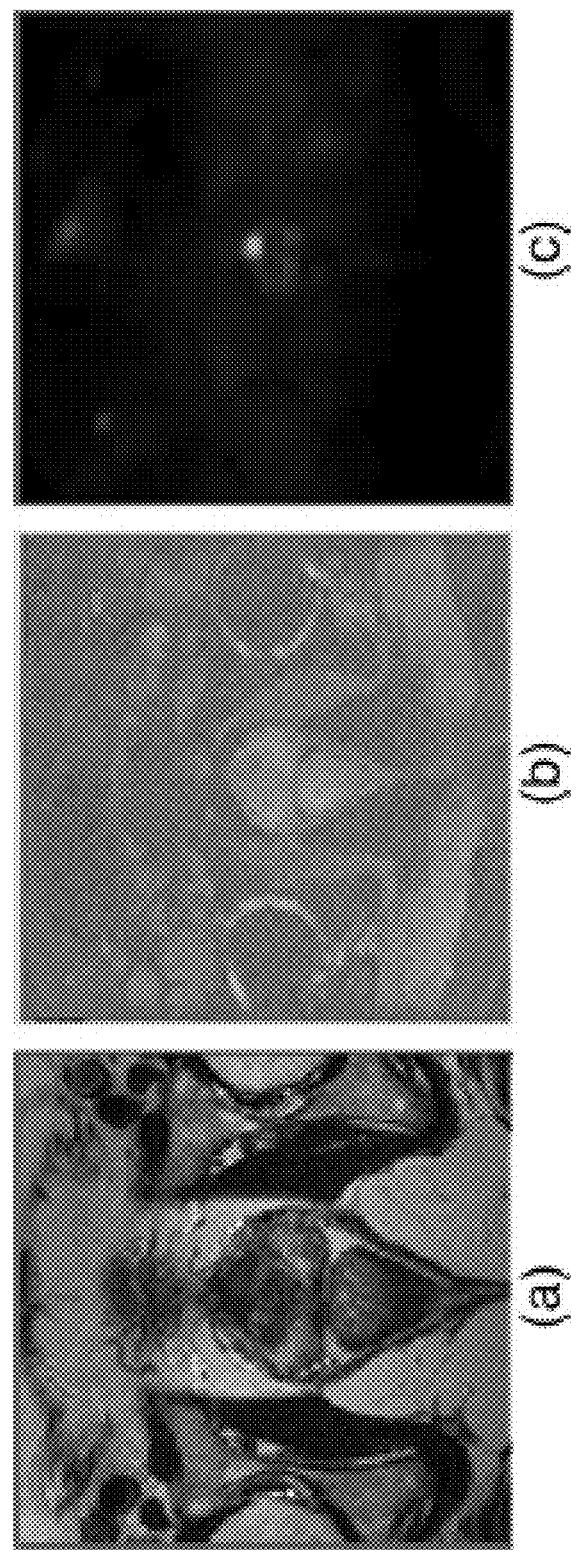
FIGS. 5(a) and 5(b) show another illustrative example of prior art digital imaging techniques, in comparison to FIG. 5(c) which shows an illustrative digital image acquired through CDI in accordance with an embodiment.

To visualize the diagnostic performance for all patient cases, ROC curves for CDI and ADC map results from all patient cases are shown in FIG. 3. It can be observed that improved ROC characteristics are exhibited by CDI when compared to an ADC map. Furthermore, the area under the ROC curve for CDI is higher with $A_z$=0.9789, compared to the ROC curve for ADC map with $A_z$=0.9183. The overall sensitivity, specificity, and accuracy results from the LOOCV trials are shown in Table 1, below.

TABLE 1

Leave-one-out cross-validation (LOOCV) results

|  | Sensitivity | Specificity | Accuracy |
| --- | --- | --- | --- |
| CDI | 0.8676 | 0.9444 | 0.9363 |
| ADC | 0.8236 | 0.7679 | 0.7691 |

It can be observed that the sensitivity, specificity, and accuracy are higher for CDI when compared to ADC, which indicates the potential usefulness of CDI as an imaging modality for building computer-aided clinical decision support systems to assist in the prostate cancer detection and localization process.

Figure 6:
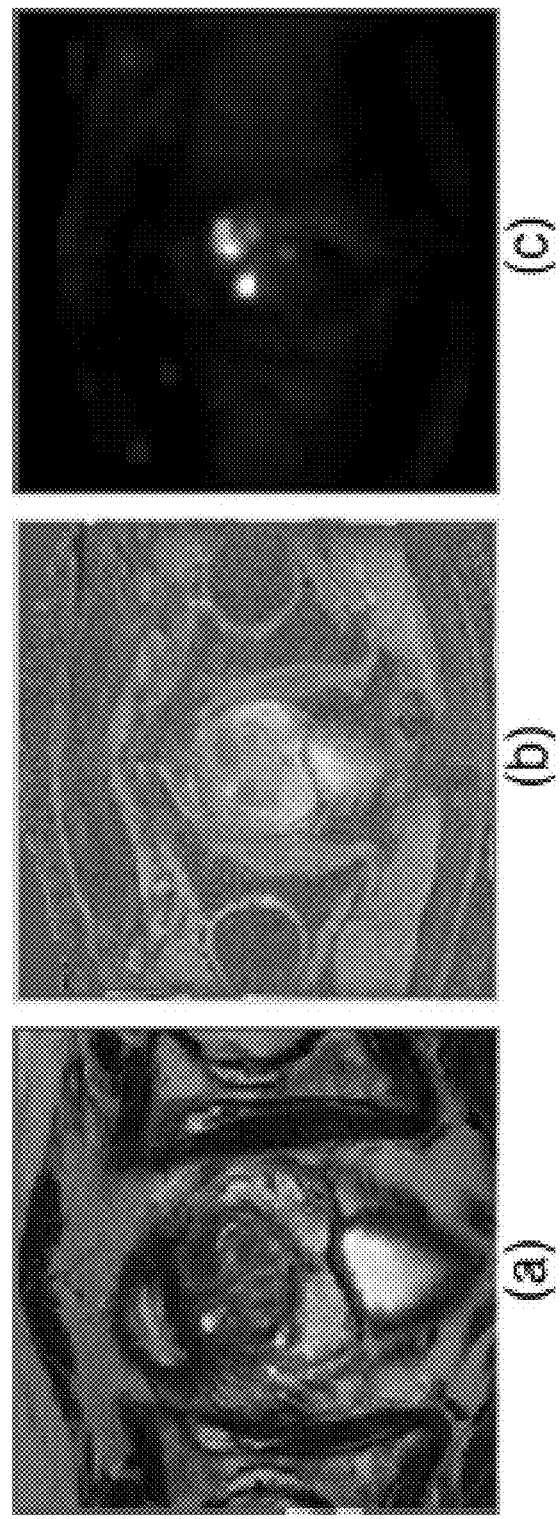
FIGS. 6(a) and 6(b) show another illustrative example of prior art digital imaging techniques, in comparison to FIG. 6(c) which shows illustrative digital images in accordance with an embodiment.
FIG. 6(d) shows an illustrative example of a digital image acquired through CDI overlaid on a T2-weighted image, in which the potentially cancerous tissue is highlighted in a different color.
Figure 6D:

FIGS. 4(a)-4(c), 5(a)-5(c), and 6(a)-6(c) show illustrative examples of slices from T2-weighted imaging, ADC map, and CDI of three patient cases out of the twenty patient cases used in the ROC analysis, and a number of observations can be made. Note that example slices show cancerous regions within the prostate gland, not benign prostatic hyperplasia (BPH) nodules. There is weak visual delineation between prostate cancer and healthy tissue in the prostate gland in the T2-weighted imaging, thus making it difficult even for highly-qualified subspecialty radiologists to interpret (particularly in FIGS. 4(a) and 4(b) and 5(a) and 5(b) where there is no decrease in signal in the cancerous region). The ADC map provides improved visual delineation compared to the T2-weighted imaging; however, it can be observed that there are some cases (e.g., FIGS. 6(a) and 6(b)) where the boundary delineation between tumor and healthy tissue is still difficult to assess. In contrast, the results obtained from using correlated diffusion imaging or CDI in accordance with the present invention is shown in FIG. 6(c). As can be seen, FIG. 6(c) provides a much clearer indication of the locations and boundaries of the prostate cancer compared to the ADC maps for all patient cases. Hence, these experimental results are very promising and motivating for the potential of CDI as a diagnostic tool for prostate cancer detection and localization.

Discussion

In this disclosure, a new form of diffusion magnetic resonance imaging has been introduced called correlated diffusion imaging or CDI, which quantifies joint correlation in signal attenuation across multiple diffusion gradient pulse strengths and timings. The experimental results in the study evaluating the performance of CDI show that CDI can be an effective tool for prostate cancer detection and localization.

However, it is also important to understand the merits of CDI in relation to practical aspects of clinical image acquisition, post-processing, and analysis. One of the attractive characteristics of CDI from a clinical image acquisition perspective is that the signal acquisition process of CDI can be performed on existing clinical imaging systems without hardware modifications, although the signal mixing process of CDI can also be built in hardware for integration into clinical imaging systems. The signal mixing and reconstruction process of CDI can all be performed post-acquisition on a computer workstation using additional computer-aided clinical decision support software such as the ProCanVAS (Prostate Cancer Visualization and Analysis System) platform developed at the University of Waterloo Vision and Image Processing research group. Once reconstructed, the CDI images can be viewed on any existing DICOM viewer software, making it easy to integrate into existing radiology workflows.

One possible explanation for CDI's potential to be a more effective tool for prostate cancer detection and localization when compared to standard clinical practice ADC maps may be related to the highly restrictive water diffusion nature of prostate cancer. While different gradient pulse strengths and timings may be more sensitive to different degrees of water diffusion motion, this highly restrictive diffusion nature results in signal attenuation that is similar or lower than healthy tissue at all degrees of sensitivity. Therefore, this results in consistently low signal attenuation of prostate cancer compared with healthy tissue irrespective of gradient pulse strengths and timings which, in combination with the possible higher water content of cancerous tissue compared to healthy tissue, may lead to improved cancer and healthy tissue delineation in CDI.

Dual-Stage Signal Mixing

Figure 7:
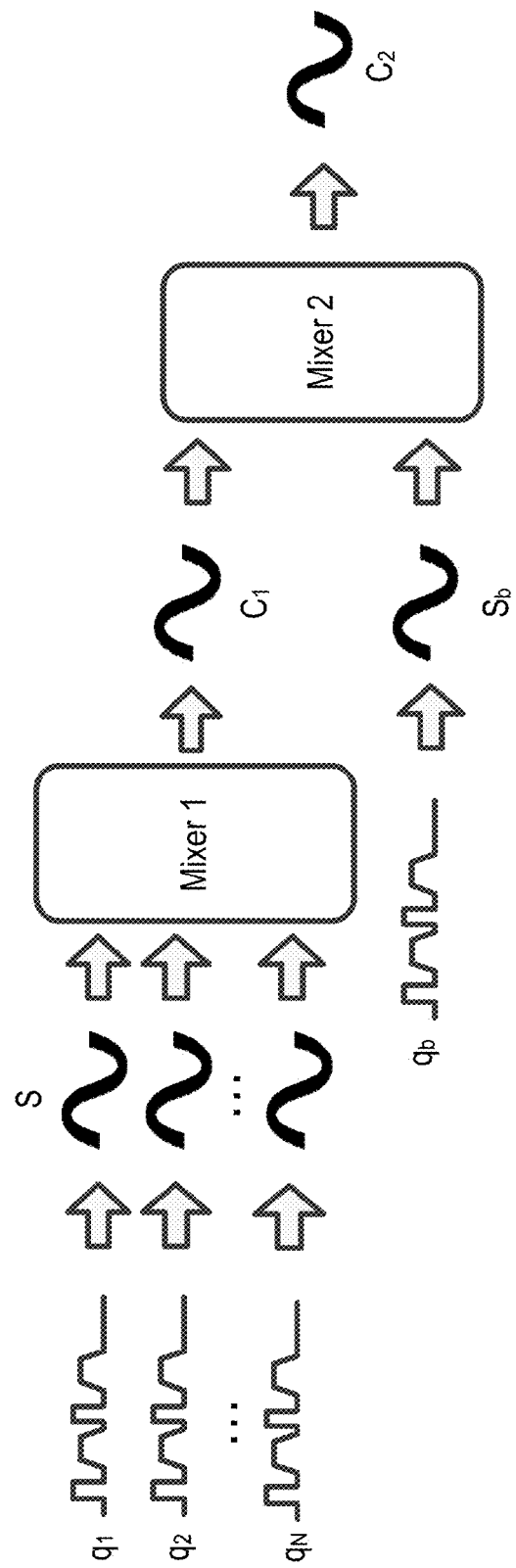
FIG. 7 is an illustrative example of a method of performing correlated diffusion imaging (CDI) in accordance with another embodiment.

FIG. 7 is an illustrative example of a method of performing correlated diffusion imaging (CDI) utilizing a dual-stage signal mixing methodology in accordance with another embodiment. In this embodiment, a dual-stage signal mixing configuration involves an additional third step of the CDI imaging process. After a step of the CDI imaging process in which multiple signal acquisitions, and any interpolated and/or extrapolated signals based on signal acquisitions, are mixed together using the first signal mixing function C(x), the output quantitative signal $C_1$ of this first signal mixing process is then mixed with a baseline signal $S_b$ (obtained in one embodiment using baseline sequence $q_b$ such as setting $q_b$=0 s/mm²) via a second signal mixing process defined by the signal mixing function $C_2(x)$:

$$C_2(x) = \int \ldots \int \exp(\tau_b S_b(x)) \exp(\tau_{C_1} C_1(x)) f(S_b(x), C_1(x), V(x)) dS_b(x) dC_1(x), \quad (4)$$

where x denotes spatial location, $S_b$ denotes the acquired baseline signal, $\tau_b$ denotes the scale factor of $S_b$, $\tau_{C1}$ denotes the scale factor of $C_1$, $f$ denotes a function that relates $S_b(x)$, $C_1(x)$ within the local sub-volume around x (denoted by V(x). In this embodiment, the function $f$ is set as the conditional joint probability (e.g., $f(S_b(x), C_1(x)|V(x))$). It will be appreciated, however, that the implementation of the present system and method is not limited to this particular function $f$, and other functions may be used for in other embodiments.

While the dual-stage mixing example as shown in FIG. 7 and described above uses an MRI signal as the baseline signal $S_b$, it will be appreciated that other types of image signals may be used, including for example computed tomography (CT) and ultrasound.

In addition, during the mixing stage, the signals that are mixed may be a combination of acquired signals, and interpolated or extrapolated signals based on acquired signals.

A key benefit of the dual-stage signal mixing configuration of CDI is that anatomical information is better visualized in the resulting output signal $C_2$ while preserving strong delineation between cancerous tissue and healthy tissue. In comparison to the single-stage signal mixing configuration of CDI, the dual-stage signal mixing configuration of CDI provides significantly better visualization of the anatomical information while providing similar delineation between cancerous tissue and healthy tissue.

Figure 8A:
FIGS. 8(a) to 8(c) show another illustrative examples of digital images acquired through the dual-stage signal mixing configuration of CDI in accordance with an embodiment in which potentially cancerous tissue is highlighted with arrows.
Figure 8B:
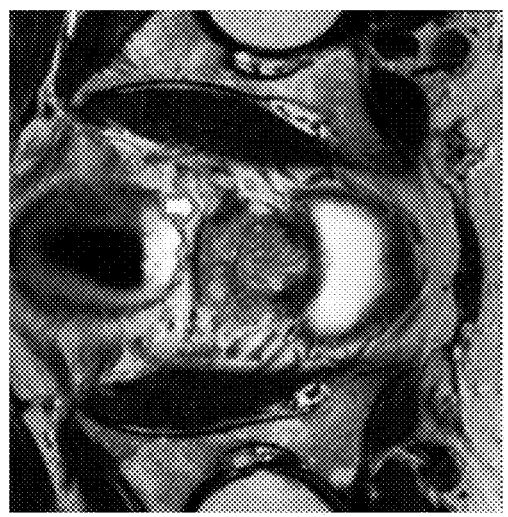
Figure 8C:

Illustrative examples of digital images acquired through the dual-stage signal mixing configuration of CDI are shown in FIGS. 8(a) to 8(c), in which potentially cancerous tissue is again highlighted with arrows.

Figure 9:
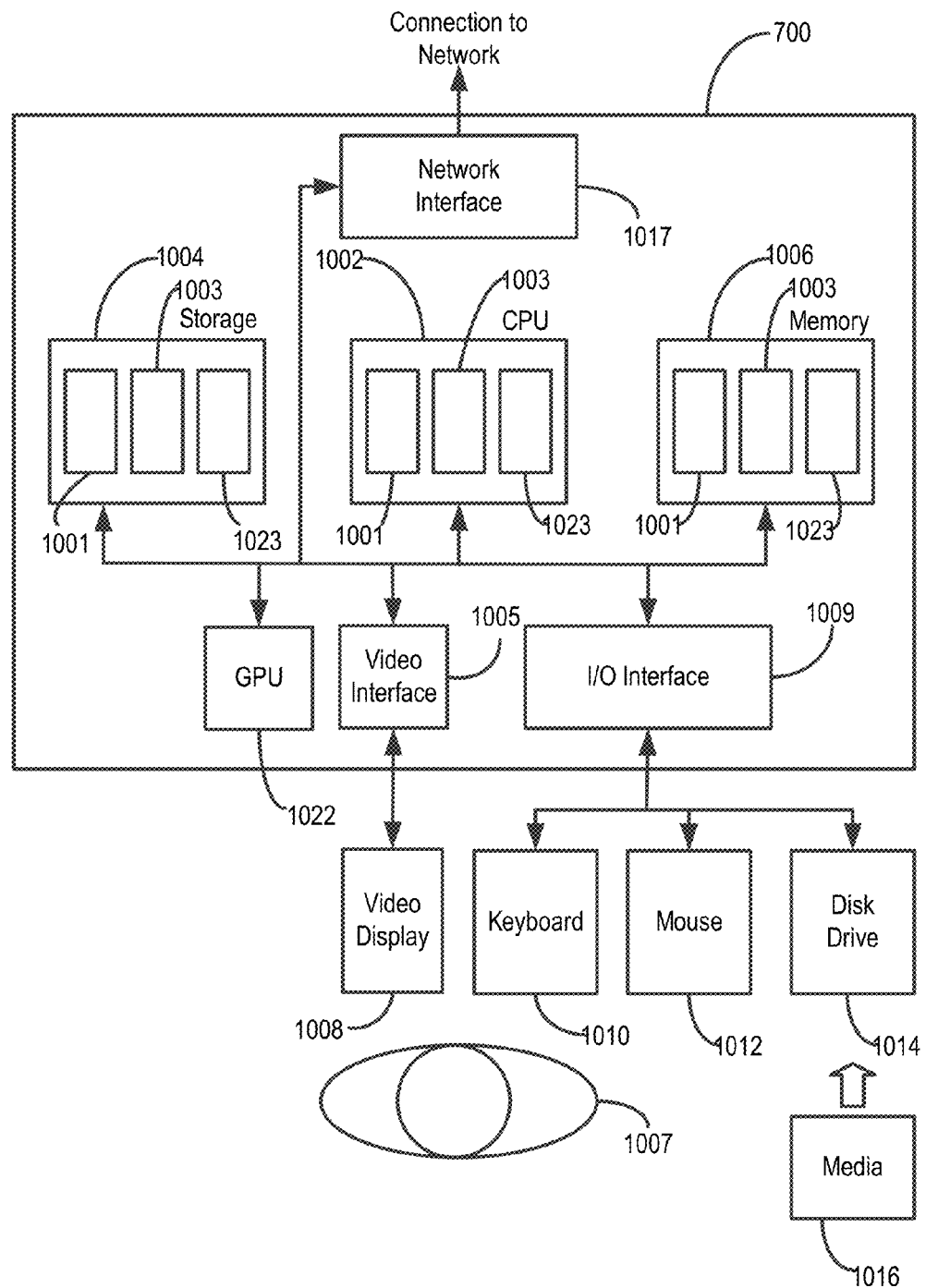
FIG. 9 shows an illustrative example of a generic computing device that may provide a suitable operating environment for one or more embodiments.

Now referring to FIG. 9, shown is a schematic block diagram of a generic computing device. A suitably configured computer device, and associated communications networks, devices, software and firmware may provide a platform for enabling one or more embodiments as described above. By way of example, FIG. 9 shows a generic computer device 1000 that may include a central processing unit ("CPU") 1002 connected to a storage unit 1004 and to a random access memory 1006. The CPU 1002 may process an operating system 1001, application program 1003, and data 1023. The operating system 1001, application program 1003, and data 1023 may be stored in storage unit 1004 and loaded into memory 1006, as may be required. Computer device 1000 may further include a graphics processing unit (GPU) 1022 which is operatively connected to CPU 1002 and to memory 1006 to offload intensive image processing calculations from CPU 1002 and run these calculations in parallel with CPU 1002. An operator 10010 may interact with the computer device 1000 using a video display 1008 connected by a video interface 1005, and various input/output devices such as a keyboard 1010, pointer 1012, and storage 1014 connected by an I/O interface 1009. In known manner, the pointer 1012 may be configured to control movement of a cursor or pointer icon in the video display 1008, and to operate various graphical user interface (GUI) controls appearing in the video display 1008. The computer device 1000 may form part of a network via a network interface 1011, allowing the computer device 1000 to communicate with other suitably configured data processing systems or circuits. One or more different types of sensors 1030 connected via a sensor interface 1032 may be used to search for and sense input from various sources. The sensors 1030 may be built directly into the generic computer device 1000, or optionally configured as an attachment or accessory to the generic computer device 1000.

Thus, in an aspect, there is provided a computer-implemented method operable on a computer device for detection and localization of tissue of interest, comprising: receiving multiple signal acquisitions of imaged tissue from a subject; mixing in a first stage the acquired signals to obtain a joint correlation of diffusion signal attenuation in dependence upon the acquired signals; and displaying on a digital display a resulting delineation of the imaged tissue of interest and background tissue based on the joint correlation of diffusion signal attenuation.

In an embodiment, the multiple signal acquisitions are obtained from one of a magnetic resonance imaging (MRI) device, a computed tomography device, and an ultrasound device.

In another embodiment, the multiple signal acquisitions measure signal attenuation of the imaged tissue at different water diffusion motion sensitivities across multiple gradient pulse strengths and timings.

In another embodiment, obtaining a joint correlation of diffusion imaging comprises performing quantitative evaluation of the multiple signals using one or more of receiver operating characteristic (ROC) curve analysis, tissue class separability analysis, and visual assessment.

In another embodiment, the method further comprises mixing in the first stage one or more interpolated or extrapolated signals based on the acquired signals.

In another embodiment, the method further comprises comparing T2-weighted imaging results with that obtained using standard diffusion imaging via an apparent diffusion coefficient ADC); and utilizing the comparison to obtain a joint correlation of diffusion signal attenuation.

In another embodiment, the method further comprises mixing in a second stage the obtained joint correlation of diffusion signal attenuation with a baseline signal containing anatomical information; and displaying the tissue of interest on the digital display, whereby the tissue of interest is delineated against a background of anatomical information to provide a visualization of the localization of the tissue of interest relative to the anatomical features of the subject.

In another embodiment, the method further comprises providing one or more user-operable controls to allow a user to interact with the computer device to modify one or more image parameters, whereby the delineation of the tissue of interest on the digital display against the background of anatomical information may be further improved.

In another aspect, there is provided a system for detection and localization of tissue of interest, the system adapted to: receive multiple signal acquisitions of imaged tissue from a subject; mix in a first stage the acquired signals to obtain a joint correlation of diffusion signal attenuation in dependence upon the acquired signals; and display on a digital display a resulting delineation of the imaged tissue of interest and background tissue based on the joint correlation of diffusion signal attenuation.

In an embodiment, the multiple signal acquisitions are obtained from one of a magnetic resonance imaging (MRI) device, a computed tomography device, and an ultrasound device.

In another embodiment, the multiple signal acquisitions measure signal attenuation of the imaged tissue at different water diffusion motion sensitivities across multiple gradient pulse strengths and timings.

In another embodiment, obtaining a joint correlation of diffusion imaging comprises performing quantitative evaluation of the multiple signals using one or more of receiver operating characteristic (ROC) curve analysis, tissue class separability analysis, and visual assessment.

In another embodiment, the system is further adapted to mix in the first stage one or more interpolated or extrapolated signals based on the acquired signals.

In another embodiment, the system is further adapted to: compare T2-weighted imaging results with that obtained using standard diffusion imaging via an apparent diffusion coefficient ADC); and utilize the comparison to obtain a joint correlation of diffusion signal attenuation.

In another embodiment, the system is further adapted to: mix in a second stage the obtained joint correlation of diffusion signal attenuation with a baseline signal containing anatomical information; and display the tissue of interest on the digital display, whereby the tissue of interest is delineated against a background of anatomical information to provide a visualization of the localization of the tissue of interest relative to the anatomical features of the subject.

In another embodiment, the system is further adapted to: provide one or more user-operable controls to allow a user to interact with the system to modify one or more image parameters, whereby the delineation of the tissue of interest on the digital display against the background of anatomical information may be further improved.

In another aspect, there is provided a computer program product comprising a computer-readable medium, the computer program product storing code executable on a computer device for detection and localization of tissue of interest, the computer program product comprising: code for receiving multiple signals acquisitions of imaged tissue from a subject; code for mixing in a first stage the acquired signals to obtain a joint correlation of diffusion signal attenuation in dependence upon the acquired signals; and code for displaying on a digital display a resulting delineation of the imaged tissue of interest and background tissue based on the joint correlation of diffusion signal attenuation.

In an embodiment, the multiple signal acquisitions are obtained from one of a magnetic resonance imaging (MRI) device, a computed tomography device, and an ultrasound device.

In another embodiment, the multiple signal acquisitions measure signal attenuation of the imaged tissue at different water diffusion motion sensitivities across multiple gradient pulse strengths and timings.

In another embodiment, the computer program product further comprises code for obtaining a joint correlation of diffusion imaging by performing quantitative evaluation of the multiple signals using one or more of receiver operating characteristic (ROC) curve analysis, tissue class separability analysis, and visual assessment.

While illustrative embodiments have been described above by way of example, it will be appreciated that various changes and modifications may be made without departing from the scope of the invention, which is defined by the following claims.

The invention claimed is:

1. A computer-implemented method operable on a computer device for detection and localization of tissue of interest, comprising:
   receiving multiple signal acquisitions of imaged tissue from a subject;
   mixing in a first stage the acquired signals;
   comparing T2-weighted imaging results with that obtained using standard diffusion imaging via an apparent diffusion coefficient (ADC);
   utilizing the comparison to obtain a joint correlation of diffusion signal attenuation; and
   displaying on a digital display a resulting delineation of the imaged tissue of interest and background tissue based on the joint correlation of diffusion signal attenuation.

2. The computer-implemented method of claim 1, wherein the multiple signal acquisitions are obtained from one of a magnetic resonance imaging (MRI) device, a computed tomography device, and an ultrasound device.

3. The computer-implemented method of claim 1, wherein the multiple signal acquisitions measure signal attenuation of the imaged tissue at different water diffusion motion sensitivities across multiple gradient pulse strengths and timings.

4. The computer-implemented method of claim 1, wherein obtaining a joint correlation of diffusion imaging comprises performing quantitative evaluation of the multiple signals using one or more of receiver operating characteristic (ROC) curve analysis, tissue class separability analysis, and visual assessment.

5. The computer-implemented method of claim 1, further comprising mixing in the first stage one or more interpolated or extrapolated signals based on the acquired signals.

6. The computer-implemented method of claim 1, further comprising:
   mixing in a second stage the obtained joint correlation of diffusion signal attenuation with a baseline signal containing anatomical information; and
   displaying the tissue of interest on the digital display, whereby the tissue of interest is delineated against a background of anatomical information to provide a visualization of the localization of the tissue of interest relative to the anatomical features of the subject.

7. The computer-implemented method of claim 6, further comprising:
   providing one or more user-operable controls to allow a user to interact with the computer device to modify one or more image parameters, whereby the delineation of the tissue of interest on the digital display against the background of anatomical information may be further improved.

8. A computer-implemented system for detection and localization of tissue of interest, the computer-implemented system having a processor and a memory adapted to:
   receive multiple signal acquisitions of imaged tissue from a subject;
   mix in a first stage the acquired signals;
   compare T2-weighted imaging results with that obtained using standard diffusion imaging via an apparent diffusion coefficient (ADC);
   utilize the comparison to obtain a joint correlation of diffusion signal attenuation; and
   display on a digital display a resulting delineation of the imaged tissue of interest and background tissue based on the joint correlation of diffusion signal attenuation.

9. The system of claim 8, wherein the multiple signal acquisitions are obtained from one of a magnetic resonance imaging (MRI) device, a computed tomography device, and an ultrasound device.

10. The system of claim 8, wherein the multiple signal acquisitions measure signal attenuation of the imaged tissue at different water diffusion motion sensitivities across multiple gradient pulse strengths and timings.

11. The system of claim 8, wherein obtaining a joint correlation of diffusion imaging comprises performing quantitative evaluation of the multiple signals using one or more of receiver operating characteristic (ROC) curve analysis, tissue class separability analysis, and visual assessment.

12. The system of claim 8, wherein the system is further adapted to mix in the first stage one or more interpolated or extrapolated signals based on the acquired signals.

13. The system of claim 8, wherein the system is further adapted to:
   mix in a second stage the obtained joint correlation of diffusion signal attenuation with a baseline signal containing anatomical information; and
   display the tissue of interest on the digital display, whereby the tissue of interest is delineated against a background of anatomical information to provide a visualization of the localization of the tissue of interest relative to the anatomical features of the subject.

14. The system of claim 13, wherein the system is further adapted to:
   provide one or more user-operable controls to allow a user to interact with the system to modify one or more image parameters, whereby the delineation of the tissue of interest on the digital display against the background of anatomical information may be further improved.

15. A computer program product comprising a non-transitory computer-readable medium, the computer program product storing code executable on a computer device for detection and localization of tissue of interest, the computer program product comprising:
- code for receiving multiple signals acquisitions of imaged tissue from a subject;
- code for mixing in a first stage the acquired signals;
- code for comparing T2-weighted imaging results with that obtained using standard diffusion imaging via an apparent diffusion coefficient (ADC);
- code for utilizing the comparison to obtain a joint correlation of diffusion signal attenuation; and
- code for displaying on a digital display a resulting delineation of the imaged tissue of interest and background tissue based on the joint correlation of diffusion signal attenuation.

16. The computer program product of claim 15, wherein the multiple signal acquisitions are obtained from one of a magnetic resonance imaging (MRI) device, a computed tomography device, and an ultrasound device.

17. The computer program product of claim 15, wherein the multiple signal acquisitions measure signal attenuation of the imaged tissue at different water diffusion motion sensitivities across multiple gradient pulse strengths and timings.

18. The computer program product of claim 15, further comprising code for obtaining a joint correlation of diffusion imaging by performing quantitative evaluation of the multiple signals using one or more of receiver operating characteristic (ROC) curve analysis, tissue class separability analysis, and visual assessment.

19. A computer-implemented method operable on a computer device for detection and localization of tissue of interest, comprising:
- receiving multiple signal acquisitions of imaged tissue from a subject;
- mixing in a first stage the acquired signals to obtain a processed diffusion signal;
- mixing in a second stage the obtained processed diffusion signal with a baseline signal; and
- displaying the tissue of interest on a digital display based on the mixed processed diffusion signal and baseline signal, whereby the tissue of interest is delineated against a background of anatomical information to provide a visualization of the localization of the tissue of interest relative to the anatomical features of the subject.

20. A computer-implemented system for detection and localization of tissue of interest, the computer-implemented system having a processor and a memory adapted to:
- receive multiple signal acquisitions of imaged tissue from a subject;
- mix in a first stage the acquired signals to obtain a processed diffusion signal;
- mix in a second stage the obtained processed diffusion signal with a baseline signal; and
- display the tissue of interest on a digital display based on the mixed processed diffusion signal and baseline signal, whereby the tissue of interest is delineated against a background of anatomical information to provide a visualization of the localization of the tissue of interest relative to the anatomical features of the subject.

* * * * *